United States Patent [19]

Skoog

[11] 4,018,810
[45] Apr. 19, 1977

[54] ORGANIC DYE HAVING FLUOROALIPHATIC SUBSTITUENT

[75] Inventor: Ivan H. Skoog, Lake Elmo, Minn.

[73] Assignee: Minnesota Mining and Manufacturing Company, St. Paul, Minn.

[22] Filed: June 11, 1975

[21] Appl. No.: 586,097

[62] Related U.S. Application Data

Division of Ser. No. 300,752, Oct. 25, 1972, U.S. Pat. No. 3,933,914

[52] U.S. Cl. .................. 260/465 D; 260/465 E
[51] Int. Cl.² ......................... C07C 121/78
[58] Field of Search ............. 260/465 E, 465 D

[56] References Cited
UNITED STATES PATENTS

| | | | |
|---|---|---|---|
| 2,649,471 | 8/1953 | Williams et al. | 260/465 |
| 2,789,125 | 4/1957 | Kartinos et al. | 260/465 |

Primary Examiner—Dolph H. Torrence
Attorney, Agent, or Firm—Cruzan Alexander; Donald M. Sell; Richard Francis

[57] ABSTRACT

Dyes of the formula

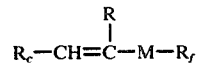

wherein $R_c$ is a monovalent chromophoric radical, M is a sulfonyl, carbonyl, or carbonyloxy bridging radical, $R_f$ is a monovalent saturated fluoroaliphatic radical, and R is a monovalent organic radical selected from cyano, $MR_f$, or aryl sulfonyl. A wide spectrum of unusually brilliant colors is available.

2 Claims, No Drawings

ORGANIC DYE HAVING FLUOROALIPHATIC SUBSTITUENT

This is a division of application Ser. No. 300,752, filed Oct. 25, 1972, now U.S. Pat. No. 3,933,914.

BRIEF SUMMARY OF THE INVENTION

This invention relates to novel synthetic organic dyes.

The dyes of the invention are basically composed of a chromophoric radical that is chemically bonded in a novel chemical arrangement to a fluoroaliphatic moiety. The presence of the fluoroaliphatic moiety in the new dye compound produces several unexpected advantages. The foremost advantage produced in many of these new chemical compounds is their narrow spectral absorbence bands, thought to be caused by the presence of the fluoroaliphatic moiety, producing dyes with extremely brilliant hues. Another unexpected advantage is the bathochromatic spectral shift, also thought to be caused by the presence of the fluoroaliphatic moiety. With such a spectral shift, it is possible to produce dyes having spectral absorbences at wave lengths longer than corresponding non-fluoroaliphatic substituted dyes. Utilizing this advantage, it is additionally possible to produce dyes ranging in color from yellow to magenta to cyan by merely extending the structure of any dye by addition of more units capable of providing chemical conjugation, e.g., C—C units, thereby producing dyes having a multitude of colors from similar reactants. Still another advantage is seen in the ability of some of the dyes of the invention to display "heat transfer" properties.

The term "heat transfer" as herein used means the ability of a mass of the dye to be transformed, from a solid or liquid state after it is heated on one surface, to a gaseous state, and to return to the previous state on another surface.

The dyes of the present invention can be used in light filters, photographic and textile dyes, and in other applications where organic dyes are presently used. The heat-transferable dyes of the invention can be used in thermographic copying processes.

DETAILED DESCRIPTION OF THE INVENTION

Briefly, the dyes of the present invention are represented by the formula

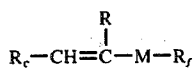

I.

wherein $R_c$ represents a monovalent chromophoric radical, M represents

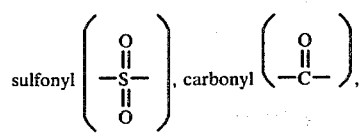

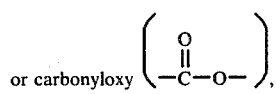

$R_f$ represents a fluoroaliphatic radical, and R represents a monovalent electron-withdrawing radical such as a cyano, arylcarbonyl, alkylcarbonyl, perfluoralkyl, alkylsulfonyl, arylsulfonyl, nitro, sulfonyl fluoride, or sulfonyl chloride radical. Radicals preferred for R include cyano, fluoroalkylsulfonyl or fluoroalkylcarbonyloxy (for example having from 1–18 carbon atoms — preferably 1–8 carbon atoms), and arylsulfonyl (preferably phenylsulfonyl).

The preferred chromophoric radicals that are represented by $R_c$ in the general formula are radicals having chemical structures shown in Formulae II–V as follows:

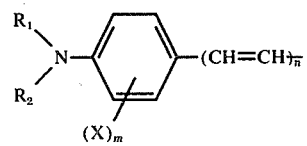

wherein $R_1$ and $R_2$ are hydrogen, monovalent alkyl (preferably methyl or ethyl), cyanoalkyl (preferably cyanomethyl or cyanoethyl), aryl (preferably phenyl), or aralkyl (preferably benzyl); $n$ is the integer 0, 1, or 2, X is halogen (preferably chlorine or bromine), lower alkyl (e.g., having 1–3 carton atoms), cyano, nitro, lower alkoxy (preferably having 1–3 carbon atoms), hydrogen, hydroxyl, sulfonate, or carboxyl; and m is the integer 1–3;

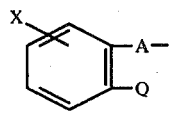

III.

wherein x is as defined above, A is a trivalent alkenylene radical having from 2–3 carbon atoms, and Q is a divalent substituted nitrogen atom such as a hydrogen, alkyl, or aryl (e.g., phenyl), substituted nitrogen, or a divalent oxygen;

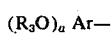

IV wherein $R_3$ is an alkyl group having from 1–4 carbon atoms, a is the integer 1–5 and Ar is a naphthylene group having a valency of $a+1$; and

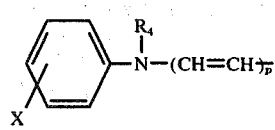

V.

wherein X is as defined above, $p$ is the integer 1–3, and $R_4$ is hydrogen or a monovalent alkyl group (preferably having from 1–3 carbon atoms).

$R_f$ is preferably a saturated fluoroaliphatic radical, for example containing 1 to 18 carbon atoms (preferably 1 to 8 carbon atoms) with the majority of the carbon atoms most preferably being perfluorinated.

The term "perfluorinated" is employed to denote substitution of all carbon-bonded hydrogen atoms by fluorine atoms, in accord with the recognized usage of the term such as may be seen in U.S. Pat. No. 2,732,398. This usage carries no implication of similarities in properties between corresponding groups and compounds of hydrocarbon and fluorocarbon systems;

hydrogen and fluorine are not chemically equivalent or similar.

The above mentioned fluoroaliphatic groups can contain chlorine atoms bonded to the carbon atoms (preferably not more than one chlorine for two adjacent carbons) as well as having fluorine and hydrogen atoms bonded to carbon atom. The fluoroaliphatic radical may be a straight or branched chain, cyclic, or a straight chain including a cyclic portion. Additionally, the fluoroaliphatic group may contain an oxygen atom linking two carbon atoms, e.g., —$CF_2OCF_2$—, or a nitrogen atom linking three carbon atoms, e.g., $(R_fCH_2)_2NCF_2$—. Exemplary fluoroaliphatic groups include 1,1,1-tris-trifluoroethyl, perfluoromethyl, perfluorobutyl, perfluorooctyl, perfluorododecyl, perfluoroisopropyl, perfluoro-(2-cyclohexylethyl), omega-chloroperfluorohexyl, 2-hydroperfluoropropyl, perfluoro(3-morpholinopropyl), and perfluoro(3-piperidinopropyl).

The dyes of the present invention may for the most part be prepared by chemical condensation of suitably substituted percursor methanes with aldehydes that contain the desired chromophoric radical. The substituted precursor methanes are characterized by having at least one methylene group that contains two reactive hydrogen atoms, i.e., that are capable of undergoing reaction with an aldehyde group to produce the condensation product. The substituted precursor methanes are also characterized by having substituents which provide the chemical functionality described above. For example, preparation of dyes having a fluoroaliphaticsulfonyl functionality, i.e., where M in Formula I is

the precursor methanes will be fluoroaliphaticsulfonyl methanes having the general formula R—$CH_2$—$SO_2$—$R_f$, where R and $R_f$ are as defined above, and most preferably the fluoroaliphaticsulfonyl methanes have the general formula $R_f'$ $SO_2CH_2SO_2R_f$ where $R_f'$ is a fluoroaliphatic radical according to the definition of $R_f$, including $R_f'$ and $R_f$ being identical. One of the simplest useful fluoroaliphaticsulfonyl methane precursors of the dyes of the invention of this type $(CF_3SO_2)_2CH_2$, is described in U.S. Pat. No. 3,586,616. Some higher homologs are described in U.S. Pat. No. 3,281,472.

For preparation of dyes having a fluoroaliphatic carbonyloxy functionality, i.e., where M in Formula I is

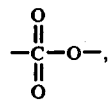

the precursor methanes will be fluoroaliphatic carbonyloxy methanes having the general formula

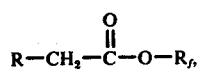

where R and $R_f$ are as defined above. Examples of useful fluoroaliphatic carbonyloxy methanes include

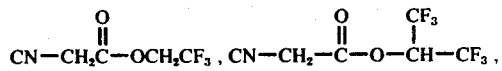

etc., which are described in assignee's copending application U.S. Ser. No. 172,603, filed Aug. 17, 1971.

For preparation of dyes having a fluoroaliphatic carbonyl functionality, i.e., where M in Formula I is

precursor methanes will have the general formula

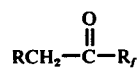

wherein R and $R_f$ are as defind above. Examples of these precursor methanes include

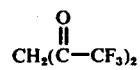

and others which are prepared according to the method describe in Henne et al, *The Alkaline Condensation of Fluorinated Esters and Ketones*, Vol. 69 JACS, pp. 1819–20 (1947).

The aldehydes with which the substituted methane precursor compounds react to form the dyes of invention may be represented by the general formula $R_c$—CHO where $R_c$ is a monovalent chromophoric radical as described above.

Aldehydes which provide the chromophoric radical, illustrated by Formula II as shown above, will have the general formula

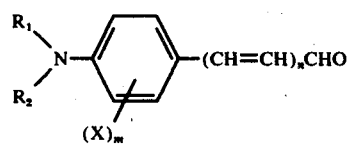

wherein $R_1$, $R_2$, X, m and n are defined above. Such aldehydes can be prepared by the method described by Vikmeir and Haak, Ber. 60, 119, (1927) or by methods outlined in U.S. Pat. Nos. 2,766,233; 2,789,125; and 3,260,737. Useful examples of this type include 4-dimethylaminobenzaldehyde, 4-diethylaminocinnamaldehyde, 4(N-methyl-N2'-cyanoethyl) aminobenzaldehyde, 2-chloro-4-dimethylaminobenzaldehyde, etc.

Likewise, aldehydes which provide the chromophoric radical, illustrated by Formula III as shown above, will have the general formula

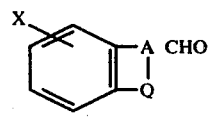

wherein X, A, and Q are as defined above. Such aldehydes are well known chemical compounds, including, e.g., β-indole aldehyde, coumarin carboxaldehyde and β-coumarone aldehyde.

Aldehydes which provide the chromophoric radical represented by Formula IV are also well known compounds; e.g., 2-methoxy-1-naphthaldehyde.

The aldehydes which provide the chromophoric radical represented by Formula V can be prepared by the method disclosed in Ann. Chem. 606, pp 79-89 (1957). An example of aldehydes of this type is 5-(N-methyl-N-phenyl)amino-2,4-pentadienal.

The chemical condensation reaction which produces the dyes of the invention through reaction of suitably substituted methane precursors and aldehydes that contain the desired chromophoric radical is of the type described in co-pending application F.N. 26,901 filed concurrently herewith by Robert J. Koshar and can be illustrated as follows:

wherein R, $R_f$ and M are as defined above.

One convenient method for preparing the dyes of this invention consists in bringing a substituted methane precursor compound into intimate contact with a suitable aldehyde in a liquid reaction medium which is non-reactive with the reactants and the product, at a suitable temperature which is generally in the range of about 20° to 150° C., and maintaining the mixture at the temperature until the reaction is essentially complete. The liquid reaction medium is preferably a solvent for the reactants but not the product, giving a convenient means of removing the product from the reaction mixture. Examples of suitable reaction media include alkanols such as ethanol, methanol and isopropanol, aromatic liquids such as benzene, toluene, xylene, mesitylene, and other liquids such as acetone, acetic acid, water, water/alkanol mixtures, and chloroform. The reaction can also proceed in the absence of a reaction medium or in a medium which merely suspends rather than dissolves the reactants. Strongly basic solutions such as aqueous sodium hydroxide or sodium methoxide are generally to be avoided because they may degrade the condensation product.

Upon completion of the reaction, the condensation product is separated from the reaction mixture, e.g., by evaporation of reaction medium or filtration, with further purification, if desired, by recrystallization of the dye.

Temperature is not a critical factor in the practice of this invention. Although the preferred range is from about 20° C. to about 150° C.; other temperatures as low as 0° C. and as high as 200° C. or even higher can be used.

The reaction, to proceed satisfactorily, may require the presence of a catalytic amount of an organic base such as piperidine, triethylamine, or the organic salt of piperidine or triethylamine. Use of a catalyst should be avoided, however, where the substituted methane precursor compound is a difluoroaliphaticsulfonyl methane. For convenience, the reactions of this invention are conducted at normal atmospheric pressure but pressures above and below atmospheric pressure can be used. The reactor can be a vessel of simple design constructed of any non-reactive materials such as glass, ceramic ware or stainless steel, and is preferably provided with means for agitation, cooling and heating.

The molar ratio of the substituted methane precursor compound to the aldehyde used in the method may be varied. Best results, however, are obtained when equimolar amounts of aldehyde and substituted methane precursor are used.

The dyes of the present invention can, as previously stated, be used in applications where conventional organic dyes are used, and because of their novel characteristics can be used in other new applications. For example, certain of the dyes can be coated, using a suitable transparent organic binder (e.g., gelatin), upon photographic film to provide a colored filter layer which can be rendered colorless during the processing of the film.

Certain of the dyes can be used to permanently dye both natural and synthetic fabrics such as fabrics made of cotton, wool, nylon, silk, polyester (e.g., Dacron), cellulose acetate (e.g., Arnel), acrylonitrile (e.g., Acrilan), viscose rayon, polyacrylonitrile (e.g., Orlon), and the like.

Certain of the dyes are also heat-transferable; therefore, they can be used in thermographic copying processes, e.g., in a color copying apparatus such as is disclosed in U.S. Pat. No. 3,601,484.

For use in thermographic copying processes the dyes are generally coated (either neat or in a suitable film-forming binder) upon a suitable carrier sheet bearing heat absorbing indicia. A receptor sheet is then stacked upon the carrier sheet and the dye-coated carrier is heated — usually by infrared heating — to cause volatization of the dye adjacent the indicia. The volatilized dye is permitted to deposit upon the surface of the receptor to produce indicia in the dye thereon. The degree of heating required to cause volatilization of the dye may vary depending upon the molecular weight of the dye and/or its chemical structure. Therefore, some experimentation may be required to determine optimum process conditions, that being within the skill of the art.

Receptors and carriers made of paper are generally preferred in the thermographic copying process but a considerable variety of other sheet goods will also function adequately, e.g., polymeric resin sheets such as polyester, polyethylene, polyperfluoroethylene, etc., metal sheets such as aluminum, copper, steel, etc., inorganic non-metallic materials such as glass, ceramic, etc.

Useful film-forming binders include normally solid organic polymeric materials and organic compounds which are transparent to infra-red radiation. Suitable binders include nitrocellulose; Saran resins; Bakelite resins (i.e., polyvinyl chloride, polyvinyl acetate, and copolymers thereof); polymethylmethacrylates; polyethylmethacrylates; polyvinyl alcohol/vinyl acetate/vinyl chloride copolymers; silicone resins; fluorocarbon resins. A preferred binder is a 1,1-dihydroperfluorooctyl-methacrylate homopolymer containing about 0.5% acrylic acid. Concentrations of dyes in the binders will vary, of course, depending upon their mutual compatibility.

The dyes are usually coated on the carrier surface from a solvent solution. The solvent is an organic liquid that is chemically inert with respect to the dye and carrier and evaporates at a reasonable low temperature, e.g., preferably less than 100° C. Useful organic solvents include alkanols such as methanol, ethanol or propanol, aromatic liquids such as benzene, toluene or xylene, and others such as acetone, chloroform etc.

The dye can be dissolved in any convenient concentration in the solvent, depending upon the application and the solubility of the dye. The concentration of dye in the coating composition for most applications will be from 0.1% to about 25% by weight.

Illustrative Examples

EXAMPLE 1

To a moderately stirred solution consisting of 1.75 g. (0.01 mole) of p-dimethylaminocinnamaldehyde dissolved in about 5 ml. of isopropyl alcohol, contained in an open glass vessel equipped with a stirrer, was slowly added a solution consisting of 2.8 g. (0.01 mole) bis(-trifluoromethylsulfonyl) methane, causing immediate precipitation of a purple solid. The contents of the flask were heated for about ten minutes; thereafter, heating was terminated and the flask contents allowed to cool to room temperature, causing additional precipitation. The purple solid was collected by filtration, recrystallized from acetonitrile and dried, giving 3.97 g. of purple dye having the formula

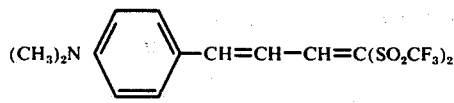

and the following properties:
Absorbence maximum (in methanol) 537 /m/$\mu$
Melting point 205°–207° C.

Thermographic Imaging

A sheet of white bond paper having black infrared absorbing printing thereon was soaked in a dilute solution (about 1%) of the dye in methyl alcohol, dried in air to remove the methyl alcohol, and stacked on a sheet of undyed unprinted bond paper of the same type as the sheet described above. The stacked sheets were passed through a thermographic copy device having an elongate infrared heat source to cause heating of the dyed sheet. Heating caused dye to transfer from the printed areas of the dyed sheet to the undyed bond sheet, producing a copy of the print in brilliant magenta on the undyed sheet. No dye transferred from the unprinted areas of the dyed sheet.

Fabric Dyeing

A small piece of Dacron polyester fabric was dyed by immersing it into a dye solution prepared as follows: 0.25 g. of the above-described dye was dissolved in 60 ml. $CH_3OCH_2CH_2OH$ with moderate heating which solution was then dissolved in 450 ml. water containing 0.25 g. sodium alkylnaphthalene sulfonate (Alkanol B) and an additional 50 ml. $CH_3OCH_2CH_2OH$. The fabric-containing solution was boiled and stirred for 10 minutes, after which time the fabric was removed, washed with aqueous detergent, rinsed and dried, producing a magenta dyed fabric.

EXAMPLES 2–35

Using a procedure similar to that set forth in Example 1 (unless otherwise specified), the following dyes according to the invention were prepared. The reactants used to prepare each of the dyes will become apparent upon seeing the chemical structure of the dye; therefore, for the sake of brevity, the chemical structures of the reactants are not shown.

| No. | Dye | Absorbence Max (m /$\mu$) (in Methanol) | Color | Melting Point (° C.) |
| --- | --- | --- | --- | --- |
| 2. | $CH_3O$-naphthalene-$CH=C(SO_2CF_3)_2$ | — | yellow | — |
| 3. | $(C_6H_5-CH_2)_2N-C_6H_4-CH=C(SO_2CF_3)_2$ | — | yellow | — |
| 4. | $(CH_3)_2N-C_6H_3(COOH)-CH=CHCH=C(SO_2CF_3)_2$ | — | magenta | — |
| 5. | indole-$CH=C(SO_2CF_3)_2$ | 402 | yellow | 257 |

-continued
| No. | Dye | Absorbence Max (m/μ) (in Methanol) | Color | Melting Point (° C.) |
|---|---|---|---|---|
| 6. | 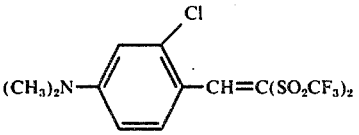 | 453 | yellow | 168–169 |
| 7. | 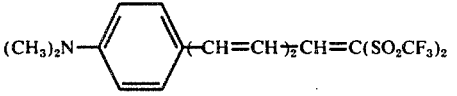 | 627 | cyan | 190–191 |
| 8. | 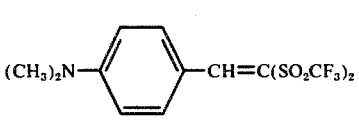 | 448 | yellow | — |
| 9. | 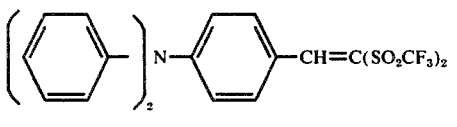 | — | yellow orange | — |
| 10. | 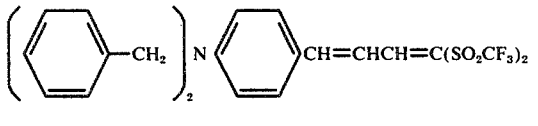 | 535 | magenta | — |
| 11. | 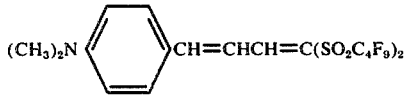 | — | magenta | — |
| 12. | 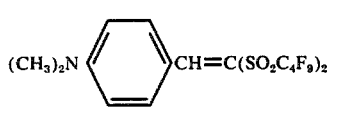 | 461 338 | yellow | 119–120 |
| 13. | 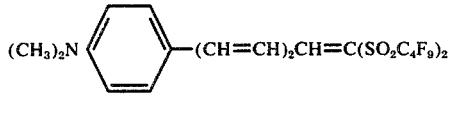 | 638 | cyan | 158–160 |
| 14. | 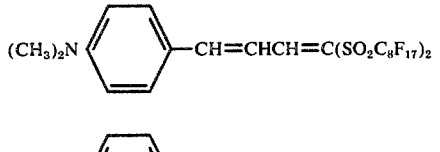 | 548 | magenta | 186–187 |
| 15. | 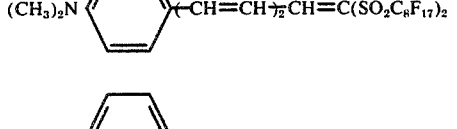 | — | cyan | 75–77 |
| 16. | 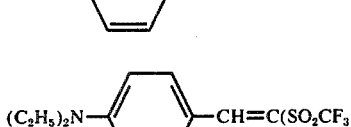 | — | yellow | 113–114.5 |
| 17. | 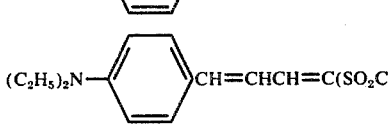 | 453 | yellow | 153 |
| 18. |  | 543 | magenta | 132–133 |

| No. | Dye | Absorbence Max (m/μ) (in Methanol) | Color | Melting Point (° C.) |
|---|---|---|---|---|
| 19. | 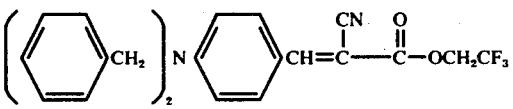 | 420 | yellow | oil |
| 20. | 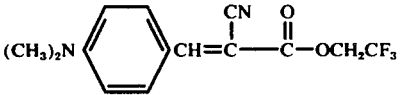 | — | yellow | 149–150 |
| 21. | 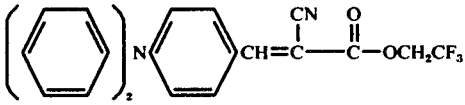 | — | orange-yellow | — |
| 22. | 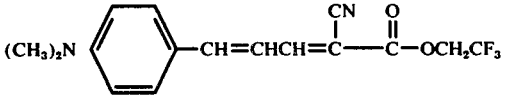 | 477 | orange | — |
| 23. | 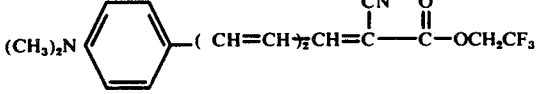 | — | red | 188–190 |
| 24. |  | 482 | orange | 154–155 |
| 25. | 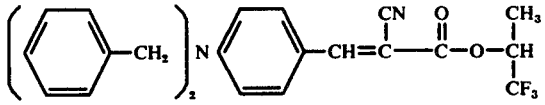 | 423 | yellow | — |
| 26. | 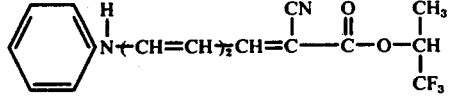 | — | magenta | — |
| 27. | 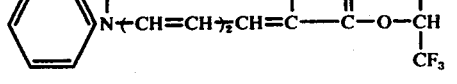 | 545 | magenta | — |
| 28. | 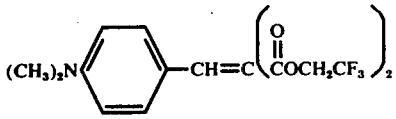 | — | yellow orange | — |
| 29. | 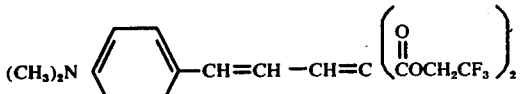 | — | red | — |
| 30. | 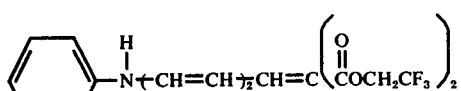 | — | orange-red | — |
| 31. | 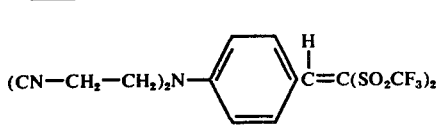 | 436 | yellow | 153–7 |

-continued

| No. | Dye | Absorbence Max (m /μ) (in Methanol) | Color | Melting Point (° C.) |
|---|---|---|---|---|
| 32. | CN—CH$_2$—CH$_2$—N(CH$_3$)—C$_6$H$_4$—C(H)=C(SO$_2$CF$_3$)$_2$ | — | yellow | 147–149 |
| 33. | (C$_6$H$_4$(SO$_3$H)—CH$_2$)$_2$N—C$_6$H$_4$—CH=C(SO$_2$CF$_3$)$_2$ | — | yellow | — |
| 34. | (CH$_3$)$_2$N—C$_6$H$_4$—CH=CH—CH=C(C(O)—CF$_3$)$_2$ | — | red-brown | 136–7 |

1,1,1,5,5,5-hexafluoro-2,4- pentanedione (0.48 g.) and N,N-dimethylaminocinnamaldehyde (0.35 g.) were dissolved with heating in 5 ml. of isopropyl alcohol to produce a yellow solution to which was added 5 drops of piperidine which caused the yellow solution to turn dark reddish-blue. After 5 minutes of additional heating, the solution was cooled to cause precipitation of a reddish-brown lustrous solid weighing 0.23 g. on drying. The solid had the chemical structure shown above.

Prepared according to the method described in Example 35.

This dye was used as a filter dye by first dissolving 0.2 grams of dye in 8 ml. of warm water and adding 3 to 12 grams aqueous gelatin and 1 ml. aqueous sodium alkylnaphthalene sulfonate (Alkanol B), coating the solution on cellulose triacetate film base, and permitting the coating to dry to a non-tacky state by solvent evaporation. The coated base film was then color processed in the usual manner using a developer consisting of 800

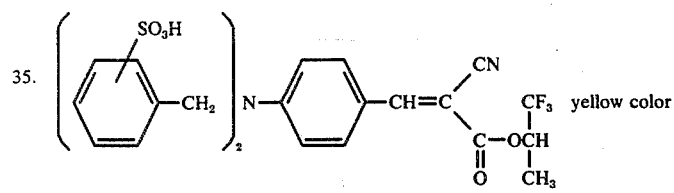

35.

Sulfonated p-dibenzylaminobenzaldehyde (0.69 g.) and 1'-trifluoromethylethyl cyanoacetate (0.40 g.) were dissolved in 50 ml. of methyl alcohol containing 12 drops of piperidine. The resultant yellow solution was refluxed for about 5 minutes and then cooled. Saturated potassium acetate solution (2 ml.) was added to cause precipitation of 0.87 g. (on drying) of the yellow dye shown above.

ml. water 1.8 g. sodium sulfate, 1.4 g. sodium bromide, 5 grams of N,N-diethylaminoaniline hydrochloride, 12.5 g. sodium hydroxide and 58 g. sodium tetraborate decahydrate (borax), and a hardener consisting of 5.0 g. sodium bisulphite, 20 ml. formalin, 3.8 g. sodium tetraborate decahydrate (borax), 4.5 g. sodium hydroxide and sufficient water to make the volume 1 liter.

The coating became colorless after 4 minutes of processing in the developer solution. Subsequent washing and drying gave a colorless film strip.

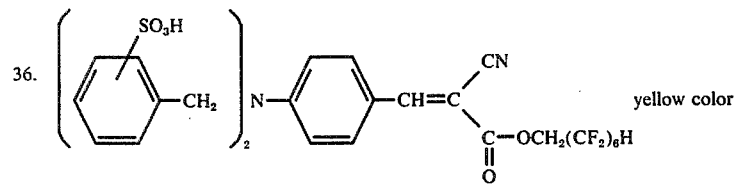

36.

| No. | Dye | Absorbence Max (m/μ) (in Methanol) | Color | Melting Point (° C.) |
|---|---|---|---|---|
| 37. | 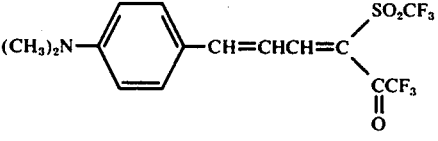 | In acetonitrile 550 m/μ | Magneta | 134–136 |
| 38. | 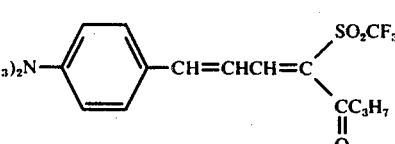 | 510 | red | 89–90 |
| 39. | 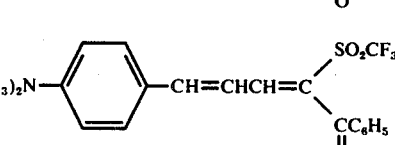 | 488 | red-orange | 122–124 |
| 40. | 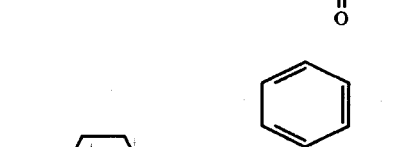 | 560 | violet | 148.5–149.5 |
| 41. | 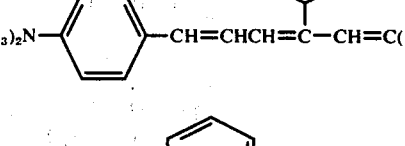 | — | red-orange | 136.5–138 |

What is claimed is:

1. A compound having the general formula

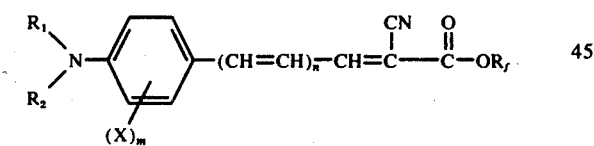

wherein $R_1$ and $R_2$ are hydrogen, alkyl, haloalkyl, aryl, or aralykl, n is the integer zero, 1 or 2, X is hydrogen, halogen, alkyl, cyano, nitro, alkoxy, —$SO_3H$, or carboxylic acid, and m is the integer 1 to 3, $R_f$ is a monovalent saturated fluoroaliphatic radical selected from the group consisting of

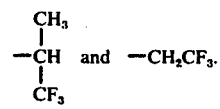

2.

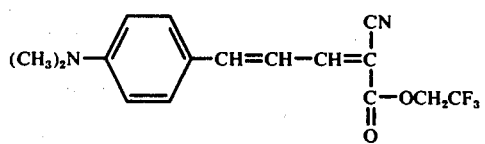

* * * * *